(12) United States Patent
Li et al.

(10) Patent No.: US 12,311,348 B2
(45) Date of Patent: May 27, 2025

(54) CATALYST PRE-HYDROCARBON POOLING METHOD AND DEVICE THEREFOR

(71) Applicant: Luoyang Weida Petrochemical Engineering Co., LTD, Henan (CN)

(72) Inventors: Qunzhu Li, Henan (CN); Ruiyun Li, Henan (CN); Li Li, Henan (CN)

(73) Assignee: Luoyang Weida Petrochemical Engineering Co., LTD, Luoyang (CN)

( * ) Notice: Subject to any disclaimer, the term of this patent is extended or adjusted under 35 U.S.C. 154(b) by 400 days.

(21) Appl. No.: 17/775,516

(22) PCT Filed: Nov. 9, 2020

(86) PCT No.: PCT/CN2020/127547
§ 371 (c)(1),
(2) Date: May 9, 2022

(87) PCT Pub. No.: WO2021/089048
PCT Pub. Date: May 14, 2021

(65) Prior Publication Data
US 2022/0401943 A1  Dec. 22, 2022

(30) Foreign Application Priority Data
Nov. 9, 2019 (CN) .......................... 201911091105.1

(51) Int. Cl.
*B01J 38/56* (2006.01)
*B01J 8/24* (2006.01)
*C07C 1/20* (2006.01)

(52) U.S. Cl.
CPC ................. *B01J 38/56* (2013.01); *B01J 8/24* (2013.01); *C07C 1/20* (2013.01)

(58) Field of Classification Search
CPC .... B01J 38/56; B01J 8/24; B01J 2208/00017; B01J 2208/00548; B01J 2208/00557;
(Continued)

(56) References Cited

U.S. PATENT DOCUMENTS 6,166,282 A   12/2000  Miller
2005/0124838 A1   6/2005  Kuechler et al.
(Continued)

FOREIGN PATENT DOCUMENTS

CN   1345361 A   4/2002
CN   101696145 A   4/2010
(Continued)

OTHER PUBLICATIONS

International Search Report from International Patent Application No. PCT/CN2020/127547, mailed Feb. 7, 2021.

*Primary Examiner* — Prem C Singh
*Assistant Examiner* — Francis C Campanell
(74) *Attorney, Agent, or Firm* — Nitin Kaushik

(57) ABSTRACT

Disclosed are a catalyst pre-hydrocarbon-pooling method and a pre-hydrocarbon-pooling device, relating to the technical field of preparation of low carbon olefins. A regenerated catalyst enters a pre-hydrocarbon-pooling reactor, and a pre-hydrocarbon-pooling reaction occurs between the regenerated catalyst and an activation medium to form "hydrocarbon pool" active species. "Pre-hydrocarbon-pooling" treatment is performed on the regenerated catalyst by providing a pre-hydrocarbon-pooling device, so that the regenerated catalyst forms the "hydrocarbon pooled" active species and carbon deposition before entering into an oxygenate conversion reactor, by way of which "hydrocarbon pool" active species distribution and coke distribution of the catalyst in the conversion reactor are improved. This shortens or eliminates a reaction "induction period" and improves the catalytic activity and selectivity of the regenerated catalyst for a reaction of an oxygenate to low-carbon olefins.

19 Claims, 2 Drawing Sheets

(58) Field of Classification Search
CPC ... B01J 29/40; B01J 29/85; B01J 29/90; B01J 38/02; B01J 38/12; B01J 37/00; B01J 37/08; B01J 8/1836; B01J 38/00; B01J 8/26; C07C 1/20; C07C 1/24; C07C 2529/85
USPC ............................................ 502/31; 585/639
See application file for complete search history.

(56) References Cited

U.S. PATENT DOCUMENTS

| | | |
|---|---|---|
| 2006/0025646 A1 | 2/2006 | Fung et al. |
| 2018/0021769 A1* | 1/2018 | Li .............................. B01J 8/20 585/469 |

FOREIGN PATENT DOCUMENTS

| | | | |
|---|---|---|---|
| CN | 102295506 A | 12/2011 | |
| CN | 111004077 A | 4/2020 | |
| CN | 111018646 A | 4/2020 | |
| CN | 111099945 A | 5/2020 | |

* cited by examiner

CATALYST PRE-HYDROCARBON POOLING METHOD AND DEVICE THEREFOR

FIELD OF THE INVENTION

The present invention relates to a method and a device for improving the selectivity of conversion of oxygenates to low-carbon olefins, and in particular, to a catalyst pre-hydrocarbon pooling (or pre-activation) method and a device therefor.

BACKGROUND OF THE INVENTION

Low-carbon olefins, defined herein as ethylene and propylene, are important basic organic chemical raw materials. In recent years, people have begun to vigorously develop alternative energy conversion technologies, such as the oxygenates-to-olefins (OTO) process. Oxygenates include methanol, ethanol, dimethyl ether, methyl ethyl ether, etc. Due to the wide range of sources of oxygenates, coupled with the cost effectiveness of using them in producing low-carbon olefins, more and more attention is being paid to the OTO process, especially the methanol-to-olefins (MTO) process.

Organic oxygenates, represented by methanol or dimethyl ether, are mainly produced from coal-based or natural gas-based synthesis gases. At present, processes for producing low-carbon olefins (mainly ethylene and propylene) with oxygenates (represented by methanol) as raw materials mainly include the MTO technology of U.S. UOP/Hyro company, the dimethyl ether/methanol-to-olefins (DMTO) technology of Dalian Institute of Chemical Physics, Chinese Academy of Sciences, and the methanol-to-propylene (MTP) technology of German Lurgi company. The methanol-to-low-carbon-olefins process (referred to as MTO) is characterized by rapid reaction, strong heat release, low catalyst-to-methanol ratio, and reaction and regeneration in a continuous reaction-regeneration dense-phase fluidized bed reactor. High-temperature oil and gas rich in low-carbon olefins such as ethylene and propylene generated by the reaction need to be quenched and washed with water, and sent, after being removed of a catalyst entrained therein and being cooled, to a downstream olefin separation system for separation. Target products of the MTO process and unit are ethylene and propylene, and by-products thereof are ethane, propane, C5+ components, and fuel gases (dry gases), and the carbon-based yield of $C_4^=$ is about 10%.

In recent years, MTO has become a hot spot and focus of research of industry insiders. Extensive research and exploration have been carried out in terms of processing flows, catalysts, process conditions, equipment structures, etc., with satisfactory results having been achieved, but there are few literature reports on how to improve the selectivity to low-carbon olefins.

As to the MTO technology, a certain amount of coke deposited on the SAPO-34 catalyst can greatly improve the yield of low-carbon olefins in reaction products (and the selectivity to low-carbon olefins is the highest when the coke deposited is in an optimal range). It is therefore necessary to properly control the amount of the coke deposited on the catalyst entering a conversion reactor, so as to achieve the purpose of improving the selectivity to low-carbon olefins. In addition, for a catalyst for which an optimal amount of coke deposited thereon exists, the more uniform the coke is distributed in a catalyst bed, the higher the selectivity to low-carbon olefins is in products. How to realize the control of uniform distribution of coke deposited on a catalyst in an MTO reactor (zone) is therefore one of the keys to the improvement of the selectivity to low-carbon olefins.

U.S. Patent No. 2006/0025646 relates to a method for controlling the amount of coke deposited on a catalyst in a reaction zone of an MTO reactor, according to which a portion of the coked catalyst (namely the spent catalyst) is passed to a regeneration zone to burn off the coke to form a regenerated catalyst, and the other portion of the coked catalyst is mixed with the regenerated catalyst and then returned to the conversion reaction zone for continued reaction. In this method, however, the coke-difference between the two catalysts entering the riser reactor is so huge that the distribution of coke on the catalyst in the reactor is very uneven. In a reactor, both a catalyst with much coke thereon and a catalyst with little coke thereon are unfavorable for the selectivity to low-carbon olefins, and may lead to decreased selectivity to low-carbon olefins and a decreased yield of target products (low-carbon olefins).

U.S. Patent No. 6,166,282 discloses a method for converting methanol to low-carbon olefins, in which a fast-fluidized bed reactor is used. After completion of a reaction in a low-gas velocity dense-phase zone, a reaction gas, together with a catalyst entrained therein, rises to a fast separation zone where most of the entrained catalyst is initially isolated. Due to the rapid separation of the reaction product from the catalyst, occurrence of a secondary reaction is effectively prevented. Simulation calculations show that compared with a traditional bubbling fluidized bed reactor, the fast fluidized bed reactor has a greatly reduced inner diameter and a decreased required catalyst inventory. The carbon-based yield of low-carbon olefins according to this method is usually about 77%. The method also has the problem of low yield of low-carbon olefins.

The DMTO technology of Dalian Institute of Chemical Physics, Chinese Academy of Sciences employs a turbulent bed reactor which is operated at a relatively low gas velocity, usually 0.6-1.0 m/s. The carbon-based yield of low-carbon olefins according to this method is generally 78-80%.

In each of the above processes, the coke-difference between the regenerated catalyst entering the conversion reactor and the catalyst in the conversion reactor is very great (in a reactor, however, both a catalyst with much "carbon" thereon and a catalyst with little "carbon" thereon are unfavorable for the selectivity to low-carbon olefins). The above processes all have problems of poor selectivity to low-carbon olefins and low yield of low-carbon olefins.

Enormous research has shown that the MTO process follows the hydrocarbon pool mechanism, and active species in the hydrocarbon pool may be olefin species, aromatic species, or both of them play a role simultaneously. With an increase in the hydrocarbon pool active species in the molecular sieve, the shape-selective effect is enhanced; the activity of the reaction is significantly improved; and an autocatalytic property is exhibited. However, the catalytic hydrocarbon pool active species are not stable, and they may react further with olefins and the like to undergo condensed cyclization, leading to coking and deactivation of the catalyst.

In an existing regenerator, the coke-burning regeneration are usually carried out at a high temperature (550-800° C.). Research has shown that although the regenerated catalyst after the high-temperature regeneration still has "carbon", the "hydrocarbon pool" active species capable of catalyzing the conversion reaction of methanol to low-carbon olefins no longer exist after the high-temperature regeneration.

The induction period of catalyzing a conversion reaction of methanol lasts usually a few minutes, but the induction period of forming the "hydrocarbon pool" active species capable of the shape-selective reaction of methanol to low-carbon olefins lasts tens of minutes or even hundreds of minutes. The later may be several dozens of times the former. As a result, catalyst beds in circulating fluidized bed reactors (zones) have the problem of uneven distribution of "hydrocarbon pool" active species.

However, conversion of methanol to hydrocarbons is a very complex reaction process, involving tens of thousands of reactions and intermediate products, and there may be hundreds of reaction paths. There are equilibrium reactions between olefin products, between aromatic hydrocarbon products, between olefins and aromatic hydrocarbons and other hydrocarbons, and conversion reactions between them are restricted by thermodynamic equilibrium as well as kinetics. Formation and types of "hydrocarbon pool" active species are therefore restricted by thermodynamic equilibrium and kinetics. The types and quantities (or contents) of "hydrocarbon pool" active species change, i.e., as long as reaction conditions change, the types and quantities of the "hydrocarbon pool" active species change. For example, "carbon" and "hydrocarbon pool" active species generated during a conversion reaction to C4+(alkene) hydrocarbons at a high temperature (e.g., 530-600° C.) not necessarily have the catalytic activity for a conversion reaction converting to low-carbon olefins under MTO reaction conditions (e.g., 470-480° C.). "Hydrocarbon pool" active species used for catalyzing a conversion reaction of methanol to hydrocarbons and "hydrocarbon pool" active species used for catalyzing a conversion reaction of methanol to low-carbon olefins are completely different or not exactly the same.

To sum up, "hydrocarbon pool" active species in industrially used circulating fluidized bed reactors are dynamically changeable (types and quantities thereof are changeable with the change of reaction conditions (mainly reaction temperatures)), and therefore catalyst beds have problems not only in the uneven distribution of carbon deposition, but also in the uneven distribution of "hydrocarbon pool" active species, which will inevitably affect catalytic activity and selectivity of conversion reactions of methanol to low-carbon olefins, which is actually the root cause for the low yield of low-carbon olefins in MTO units. For a long time, however, the foregoing problems have not caused people's attention, and so far have NO any special research and reports.

Therefore, how to realize the uniform distribution of "hydrocarbon pool" active species in MTO reactors (zones) (especially those "hydrocarbon pool" active species capable of improving the activity and selectivity of reactions of catalyzing oxygenates to low-carbon olefins under MTO conversion reaction conditions) is one of the keys to the improvement of the selectivity to low-carbon olefins.

In addition, there is a temperature difference of several hundred degrees (usually 150-300° C.) between the high-temperature regenerated catalyst directly entering the conversion reactor and the catalyst in the conversion reactor, which may cause local overheating of the catalyst bed (the high-temperature regenerated catalyst itself and its surroundings), leading to many secondary reactions, a large amount of coke-producing, and poor selectivity to low-carbon olefins in the conversion reaction process.

It is an objective of the present invention to perform, on the precondition of ensuring a good regeneration effect, "pre-hydrocarbon pooling" treatment on a regenerated catalyst by providing a pre-hydrocarbon pooling device (or a reaction zone), by means of which the sufficient time and space may be provided for a reaction of forming "hydrocarbon pool" active species capable of the shape-selective catalyzing of a conversion reaction of an oxygenate to low-carbon olefins. As such, the regenerated catalyst, before entering a conversion reactor, forms "hydrocarbon pool" active species capable of meeting requirements for conditions of the conversion reaction and having a good activity and good selectivity for catalyzing the reaction of preparing low-carbon olefins, so as to improve the activity and selectivity of the regenerated catalyst for use in the conversion reaction of the oxygenate to low-carbon olefins, and improve the distribution of "hydrocarbon pool" active species and coke of the catalyst in the conversion reactor. The present invention also uses a regenerated catalyst cooling technology to break thermal balance of the reaction-regeneration system. By providing a regenerated catalyst cooler, the temperature at which the regenerated catalyst enters the conversion reactor is reduced, which eliminates the problem of local overheating in the conversion reactor, optimizes temperature distribution in the conversion reactor, and further improves the yield of low-carbon olefins.

SUMMARY OF THE INVENTION

A technical problem to be solved by the present invention is to perform "pre-hydrocarbon pooling" treatment on a regenerated catalyst by providing a pre-hydrocarbon pooling device (or a reaction zone) to form "hydrocarbon pool" active species meeting requirements for conditions of a conversion reaction and having a good activity and good selectivity for the reaction of preparing low-carbon olefins, so as to improve the distribution of the "hydrocarbon pool" active species and coke-deposition of the catalyst in a conversion reactor, to thereby improve the activity and selectivity of the regenerated catalyst for the conversion reaction of an oxygenate to low-carbon olefins, and shorten or eliminate the "induction period" of the conversion reaction of the oxygenate to low-carbon olefins. Another technical problem to be solved is to reduce the temperature at which the regenerated catalyst enters the conversion reactor to eliminate local overheating in the conversion reactor and optimize temperature distribution in the conversion reactor (reaction zone), so as to further improve the activity and selectivity of the regenerated catalyst for the conversion of Oxygenate to low-carbon olefins (i.e. ethylene and propylene) to thereby further improve the yield of low-carbon olefins.

The present invention provides a catalyst pre-hydrocarbon pooling (or pre-activation) method and its device. A regenerated catalyst from a regenerator enters a pre-hydrocarbon pooling device, where the regenerated catalyst contacts with an activation medium to undergo reactions such as a pre-hydrocarbon pooling reaction to form "hydrocarbon pool" active species and a certain amount of carbon deposition. The regenerated catalyst leaving the pre-hydrocarbon pooling device (referred to as "pre-hydrocarbon pooled catalyst" or "pre-hydrocarbon pooled regenerated catalyst") enters a conversion reactor for recycling.

A temperature of the regenerated catalyst after cooling is 200-630° C. (preferably 300-600° C., more preferably 360-560° C.).

Main operating conditions of the pre-hydrocarbon pooling device (reactor) are as follows: a reaction temperature of 300-600° C. (preferably 360-560° C., more preferably 400-530° C.), and contact time of less than 300 minutes (preferably 0.001-200 minutes, more preferably 10-150 minutes).

The pre-hydrocarbon pooling device (reactor) includes a regenerated catalyst inlet (including a catalyst distributor), a regenerated catalyst outlet (used for the regenerated catalyst after pre-hydrocarbon pooling), an activation medium inlet (including a distributor), an activation medium outlet, or/and a fluidizing medium inlet (including a distributor).

The pre-hydrocarbon pooling device (reactor) adopts any one, two or more of various industrially used reactors, including fluidized bed reactors, moving beds, and fixed bed reactors, or a combination thereof. The fluidized bed reactors include bubbling bed reactors, turbulent bed reactors, fast bed reactors, riser reactors, etc. The riser reactors may be various industrially used equal-diameter or variable-diameter riser reactors. Preferably, the pre-hydrocarbon pooling device (reactor) adopts a (equal-diameter or variable-diameter) low-velocity dense-phase fluidized bed having a superficial gas velocity (the ratio of the flow rate of the fluidizing medium to the cross-sectional area of the device) of less than 0.5 m/s (preferably 0.0001-0.3 m/s, more preferably 0.001-0.2 m/s).

The activation medium entering the pre-hydrocarbon pooling device (reactor) may be any one, two or more of an oxygenate raw material, a reaction product, a hydrocarbon, and other oxygenates, or a mixture thereof.

The reaction product may be a reaction gas that has not undergone a separation or has been removed of part or all entrained catalyst by a first-stage separator or multiple stages of separators (which may be cyclone separators, hydrocyclone separators, etc.), or a reaction gas that has undergone a heat-exchanging, quenching, or water washing, or a reaction gas from a downstream olefin product separation device (unit) pressurized by a reaction gas compressor, or a stripping gas (containing steam, reaction products, etc.) from a top of a sewage stripper, or any one, two or more of the foregoing, or a mixture thereof.

The hydrocarbon may be any one, two or more of products (including ethylene, propylene, ethane, propane, mixed C4, C5+ fractions, fuel gases, etc.) from the downstream olefin product separation device (unit), or a mixture thereof, or may be any one, two or more of various pure component olefins, aromatic hydrocarbons, alkanes, or a mixture thereof.

The other oxygenates may be any one, two or more of any organic oxygenates (including various alcohols, ethers, esters, aldehydes, ketones, etc.), or a mixture thereof.

The catalyst may be any industrially used catalyst, including SAPO-34, ZSM-5 molecular sieve catalysts, and the like.

The pre-hydrocarbon pooling device (reactor) may be provided outside or inside the conversion reactor, or may be in a one-piece structure with the conversion reactor, or may be connected to the conversion reactor through a conveying pipe. The specific structure, connection type, operating conditions, and control processes of the pre-hydrocarbon pooling device are very clear to those of ordinary skilled in the art, and do not constitute limitations on any specific implementation of the inventive concept of the present invention.

In order to better control the reaction temperature of the pre-hydrocarbon pooling reactor, the pre-hydrocarbon pooling reactor may be provided with an internal heat extractor or/and an external heat extractor (not shown in the figure) at an interior thereof or/and an exterior thereof, to maintain the thermal balance of the pre-hydrocarbon pooling reaction system.

The reaction temperature of the pre-hydrocarbon pooling reactor may be controlled by adjusting an amount of the catalyst returned to the pre-hydrocarbon pooling reactor, or/and a flow rate of a heat extracting medium, or/and a flow rate of the fluidizing medium, or/and other parameters.

Catalyst coolers are mature industrially used devices. The method and the device of the present invention may adopt various industrially used (including fluid catalytic cracking units, MTO units, etc.) structural forms (such as up-flow, down-flow, etc.). Catalyst conveying pipes may adopt various specific connection structures (such as internal circulation pipes, Y-shaped, U-shaped external conveying (circulation) pipes, etc.), with or without degassing (balance) pipes. The selection and control of specific structures, connection types, operating parameters (such as superficial linear velocity) of the foregoing are very clear to those of ordinary skilled in the art and do not constitute limitations on any specific implementation of the inventive concept of the present invention.

The conversion reactor may be any one, two or more of various industrially used reactors, including fluidized bed reactors, moving bed reactors, and fixed bed reactors, or a combination thereof. Preferably, the conversion reactor may be any one, two or more of various industrially used (including fluid catalytic cracking units, MTO units, etc.) fluidized bed (including bubbling bed, turbulent bed, fast bed, etc.) reactors or riser reactors, or a combination thereof. The riser reactors may be various industrially used equal-diameter or variable-diameter riser reactors.

Fluidized bed (including riser) reaction-regeneration units (including fluid catalytic cracking units, MTO units, etc.) are mature industrial processes, and various reactors, internal or external catalyst coolers (referred to also as heat extractors, including up-flow, down-flow, back-mixed external heat extractors, etc.), steam (gas) strippers, catalyst distributors, steam (gas) gas distributors, and the like used by them can all be used in the present invention. Specific structures, combination types, operations, and control processes of the foregoing, as well as the selection and use of operating conditions such as feed temperatures, reaction temperatures, reaction pressures, contact time, catalyst-methanol ratios (or catalyst-oil ratios, i.e., the ratio of the catalyst to the raw material), superficial linear velocity, etc. and catalysts are very clear to those of ordinary skill in the art, and do not constitute limitations on any specific implementation of the inventive concept of the present invention.

In the use of the method and the device of the present invention, the conversion reaction conditions are conventional conditions, and the separation of the reaction products and the regeneration of the catalyst are all carried out according to conventional methods. The spent catalyst is regenerated in the regenerator by coke-burning under conventional regeneration conditions. The regeneration temperature is usually controlled at 550-800° C. (preferably 600-730° C., more preferably 650-710° C.). The conversion reaction temperature is usually 400-560° C. (preferably 420-520° C., more preferably 450-500° C.).

The method and the device of the present invention may be applied to various industrially used (including MTO units, etc.) reaction-regeneration modes. Specific structures, combination types, operation and control processes of the foregoing are very clear to those of ordinary skill in the art, and do not constitute limitations on any specific implementation of the inventive concept of the present invention.

Compared with the existing technologies, the present invention has the following advantages.

1. The catalyst pre-hydrocarbon pooling method and device of the present invention, by providing the pre-hydrocarbon pooling device, perform "pre-hydrocarbon pooling" treatment on the regenerated catalyst, so that the regenerated catalyst forms "hydrocarbon pool" active species and carbon deposition before entering the oxygenate conversion reactor, by way of which the distribution of the "hydrocarbon pool" active species and coke deposition of the catalyst in the conversion reactor can be improved, and the "induction period" of the reaction can thus be shortened or eliminated, and the catalytic activity and selectivity of the regenerated catalyst for the conversion reaction of the oxygenate to low-carbon olefins can be improved.

2. After the pre-hydrocarbon pooling, the temperature of the regenerated catalyst is decreased, which breaks the thermal balance of the reaction-regeneration system, reduces the temperature of the regenerated catalyst entering the conversion reactor, and eliminates local overheating in the conversion reactor caused by the high temperature of the regenerated catalyst, making the temperature distribution of the bed in the conversion reactor more uniform. This enormously facilitates ideal reactions such as the conversion of the oxygenate to low-carbon olefins, and inhibits non-ideal reactions such as thermal polymerization of low-carbon olefins, thereby improving the selectivity of the reaction, further improving the yield of low-carbon olefins, and reducing the coking rate of the catalyst (i.e., the coke-difference between the regenerated catalyst and the spent catalyst).

3. After the pre-hydrocarbon pooling, the temperature of the regenerated catalyst is decreased, which reduces hydrothermal deactivation of the regenerated catalyst during conveying (before being conveyed to the conversion reactor), and improves the activity of the regenerated catalyst, and reduces consumption of the catalyst.

4. The temperature of the regenerated catalyst is decreased after the pre-hydrocarbon pooling, and the adjustment of operating conditions such as the reaction temperature of the oxygenate conversion reaction and the circulation amount of the catalyst is relatively independent and more flexible. Flexible adjustment can therefore be made based on market conditions to achieve different product distributions.

5. The low-temperature regenerated catalyst after the pre-hydrocarbon pooling may be used as a cold shock agent and directly enter a rapid separation device (including an inlet or an outlet) to achieve rapid termination of the reaction. This can suppress non-ideal reactions such as thermal polymerization of low-carbon olefins, thus further improving the yield of low-carbon olefins and reducing the coking rate of the catalyst (i.e., the coke-difference between the regenerated catalyst and the spent catalyst). This, at the same time, can also realize pre-hydrocarbon pooling reaction of the reaction gas on the regenerated catalyst, to form hydrocarbon pool active species and carbon deposition, thereby shortening or eliminating the "induction period" of the reaction, improving the activity and selectivity of regenerated catalyst (used for the reaction of preparing low-carbon carbon olefins), and further improving the yield of low-carbon olefins.

The present invention will be described in detail below with reference to the accompanying drawings. The accompanying drawings are drawn to illustrate the present invention and do not constitute limitations on any specific implementation of the inventive concept of the present invention.

DETAILED DESCRIPTION OF THE EMBODIMENTS

Figure 1:
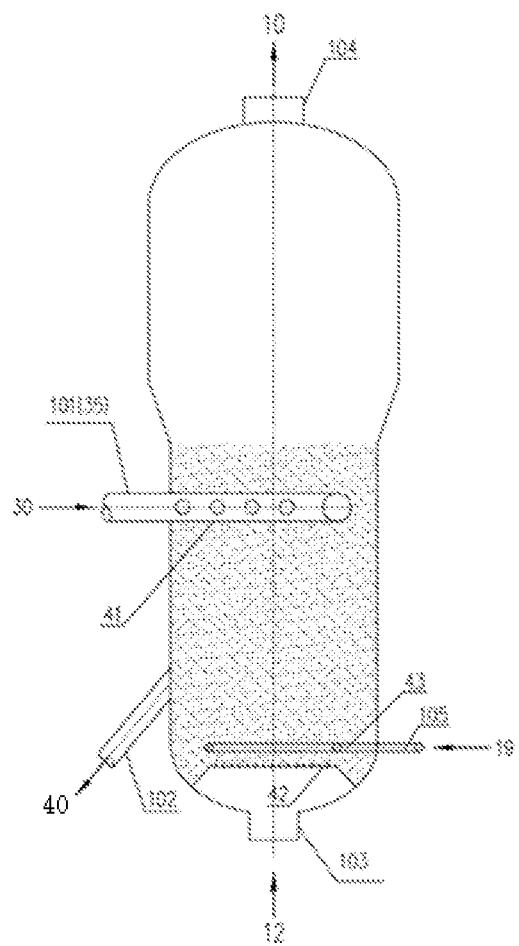
FIGS. 1 to 2 each are a schematic diagram of catalyst pre-hydrocarbon pooling (or pre-activation) method and device therefor according to the present invention.

FIG. 1 is a schematic diagram of a catalyst pre-hydrocarbon pooling (or pre-activation) method and its device according to the present invention (countercurrent contact).

As shown in FIG. 1, the catalyst pre-hydrocarbon pooling (or pre-activation) device of the present invention includes a regenerated catalyst inlet 101 (including a catalyst distributor 41), a regenerated catalyst outlet 102, an activation medium inlet 103 (including a distributor 42), an activation medium outlet 104, or/and a fluidizing medium inlet 105 (including a distributor 43).

A regenerated catalyst 30 from a regenerator enters an upper portion of a pre-hydrocarbon pooling reactor sequentially through a regenerated catalyst conveying pipe 35 (including a control valve and a catalyst distributor, not shown in the figure), the regenerated catalyst inlet 101, and the catalyst distributor 41, and flows downwardly meanwhile having a countercurrent contact with an activation medium 12 to undergo chemical reactions such as pre-hydrocarbon pooling to form "hydrocarbon pool" active species and a certain amount of carbon deposition, so as to shorten or eliminate an "induction period" of a reaction.

The activation medium 12 enters a bottom of the pre-hydrocarbon pooling reactor sequentially through the activation medium inlet 103 and the distributor 42, and passes through a regenerated catalyst bed from bottom to top. A pre-hydrocarbon pooled reaction gas 10 enters a downstream oxygenate conversion reactor (settling zone) through the activation medium outlet 104.

Alternatively, the pre-hydrocarbon pooling reactor may also be provided therein with a first-stage or second-stage cyclone separator. After the pre-hydrocarbon pooled reaction gas is removed of the catalyst entrained therein, the reaction gas enters an inlet of a third-stage cyclone separator.

A "pre-hydrocarbon pooled" regenerated catalyst 40 leaving the pre-hydrocarbon pooling reactor enters a conversion reactor through the "pre-hydrocarbon pooled" regenerated catalyst outlet 102 and a regenerated catalyst conveying pipe 33 (including a control valve and a catalyst distributor, not shown in the figure), for recycling.

In order to better control a reaction temperature of the pre-hydrocarbon pooling reactor, the pre-hydrocarbon pooling reactor may be provided at an interior or/and an exterior thereof with an internal heat extractor or/and an external heat extractor (not shown in the figure) to maintain thermal balance of the pre-hydrocarbon pooling reaction system.

The reaction temperature of the pre-hydrocarbon pooling reactor may be controlled by adjusting an amount of the catalyst returned to the pre-hydrocarbon pooling reactor, or/and a flow rate of a heat extracting medium, or/and a flow rate of a fluidizing medium, or/and other parameters.

The fluidizing medium 19 may be steam or other fluids (preferably steam). The activation medium 12 is preferably a reaction gas. The heat extracting medium may be water, steam or other fluids (preferably water).

The catalyst distributor may be any industrially used catalyst distributor, and the steam (gas) distributor may be any industrially used gas distributor (including a distribution plate, a distribution pipe, etc.).

Main operating conditions of the pre-hydrocarbon pooling reactor are as follows: a reaction temperature of 300-600° C. (preferably 360-560° C., more preferably 400-530° C.), and contact time of less than 300 minutes (preferably 0.001-200 minutes, more preferably 10-150 minutes).

The pre-hydrocarbon pooling reactor adopts a low-velocity dense-phase fluidized bed having a superficial gas velocity of less than 0.5 m/s (preferably 0.0001-0.3 m/s, more preferably 0.001-0.2 m/s).

Figure 2:
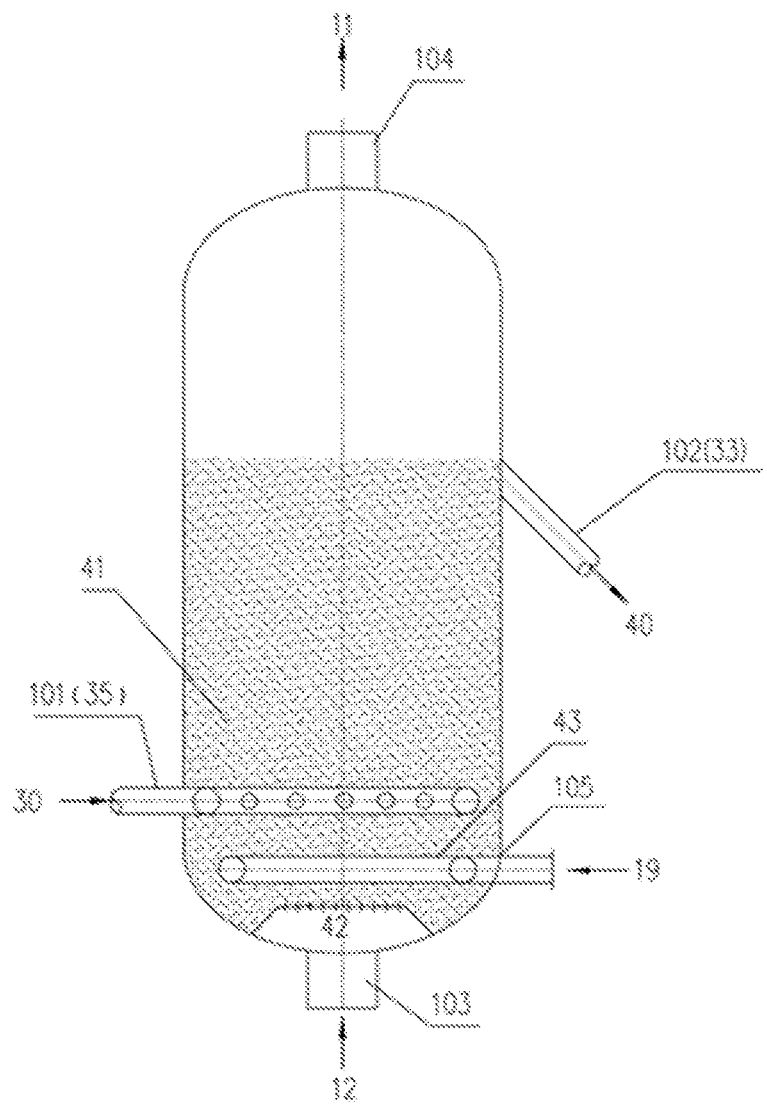

FIG. 2 is a schematic diagram of a catalyst pre-hydrocarbon pooling (or pre-activation) method and its device according to the present invention (co-current contact).

As shown in FIG. 2, the catalyst pre-hydrocarbon pooling (or pre-activation) device of the present invention includes a regenerated catalyst inlet 101 (including a catalyst distributor 41), a regenerated catalyst outlet 102, an activation medium inlet 103 (including a distributor 42), an activation medium outlet 104, or/and a fluidizing medium inlet 105 (including a distributor 43).

A regenerated catalyst 30 from a regenerator enters a bottom of the pre-hydrocarbon pooling reactor sequentially through a regenerated catalyst conveying pipe 35 (including a control valve and a catalyst distributor, not shown in the figure), the regenerated catalyst inlet 101, and the catalyst distributor 41. An activation medium 12 enters the bottom of the pre-hydrocarbon pooling reactor sequentially through the activation medium inlet 103 and the distributor 42. The regenerated catalyst 30 and the activation medium 12 flow co-currently, from bottom to top, through a regenerated catalyst bed to undergo chemical reactions such as pre-hydrocarbon pooling to form "hydrocarbon pool" active species and a certain amount of carbon deposition, so as to shorten or eliminate an "induction period" of a reaction.

A pre-hydrocarbon pooled reaction gas enters a downstream oxygenate conversion reactor (settling zone) through the activation medium outlet 104.

A "pre-hydrocarbon pooled" regenerated catalyst 40 leaving the pre-hydrocarbon pooling reactor enters a conversion reactor through the "pre-hydrocarbon pooled" regenerated catalyst outlet 102 and the regenerated catalyst conveying pipe 33 (including a control valve and a catalyst distributor, not shown in the figure), for recycling.

In order to better control a reaction temperature of the pre-hydrocarbon pooling reactor, the pre-hydrocarbon pooling reactor may be provided at an interior or/and an exterior thereof with an internal heat extractor or/and an external heat extractor (not shown in the figure) to maintain thermal balance of the pre-hydrocarbon pooling reaction system.

The reaction temperature of the pre-hydrocarbon pooling reactor may be controlled by adjusting an amount of the catalyst returned to the pre-hydrocarbon pooling reactor, or/and a flow rate of a heat extracting medium, or/and a flow rate of a fluidizing medium, or/and other parameters.

The fluidizing medium 19 may be steam or other fluids (preferably steam). The activation medium 12 is preferably a reaction gas. The heat extracting medium may be water, steam, or other fluids (preferably water).

The catalyst distributor may be any industrially used catalyst distributor, and the steam (gas) distributor may be any industrially used gas distributor (including a distribution plate, a distribution pipe, etc.).

Main operating conditions of the pre-hydrocarbon pooling reactor are as follows: a reaction temperature of 300-600° C. (preferably 360-560° C., more preferably 400-530° C.), and contact time of less than 300 minutes (preferably 0.001-200 minutes, more preferably 10-150 minutes).

The pre-hydrocarbon pooling reactor adopts a low-velocity dense-phase fluidized bed having a superficial gas velocity of less than 0.5 m/s (preferably 0.0001-0.3 m/s, more preferably 0.001-0.2 m/s).

Example 1

In Example 1, methanol is used as the oxygenate raw material, and a structure shown in FIG. 1 is adopted. The methanol conversion reactor and the regenerator are both operated under conventional conditions. SAPO-34 is used as the catalyst. A reaction gas is used as the activation medium. Main operating conditions of the pre-hydrocarbon pooling reactor are as follows: a superficial linear velocity of 0.1-0.2 m/s, a reaction temperature of 460° C., and contact time of 60-80 minutes. Here, hydrocarbon pool active species on the regenerated catalyst after pre-hydrocarbon pooling are substantially recovered and a reasonable level of carbon deposition is formed.

Simulation calculation results show that compared with the existing MTO technology, the method and the device of the present invention improve the selectivity to low-carbon olefins ($C_2^= + C_3^=$) by 5.7 percentage points.

A comparison of main parameters and effects is shown in Table 1.

TABLE 1

| Parameters | Existing MTO technology | Present invention |
|---|---|---|
| Temperature of conversion reaction ° C. | 480 | 480 |
| Temperature of regeneration ° C. | 680 | 680 |
| Catalyst/methanol ratio weight/weight | 0.23 | 0.23 |
| Coke on regenerated catalyst % | 2.3 | 2.3 |
| Regenerated catalyst cooler | No | Yes |
| Temperature of cooled regenerated catalyst ° C. | | 460-500 |
| Pre-hydrocarbon pooling device | No | Yes |
| Temperature of pre-hydrocarbon pooling reaction ° C. | | 460 |
| Selectivity to low-carbon olefins ($C_2^=$ + $C_3^=$) % | 79.8 | 85.5 |

Example 2

In Example 2, methanol is used as the oxygenate raw material, and a structure shown in FIG. 1 is adopted. SAPO-34 is used as the catalyst. The methanol conversion reactor and the regenerator are both operated under conventional conditions. A reaction gas is used as the activation medium. Main operating conditions of the pre-hydrocarbon pooling reactor are as follows: a superficial linear velocity of 0.1-0.2 m/s, a reaction temperature of 460° C., and contact time of 30-40 minutes.

Simulation calculation results show that compared with the existing MTO technology, the present invention, with the addition of the pre-hydrocarbon pooling device of the present invention, improves the selectivity to low-carbon olefins ($C_2^= + C_3^=$) by 3.1 percentage points.

A comparison of main parameters and effects is shown in Table 2.

TABLE 2

| Parameters | Existing MTO technology | Present invention |
|---|---|---|
| Temperature of conversion reaction ° C. | 480 | 480 |
| Temperature of regeneration ° C. | 680 | 680 |
| Catalyst/methanol ratio weight/weight | 0.23 | 0.23 |
| Coke on regenerated catalyst % | 2.3 | 2.3 |
| Regenerated catalyst cooler | No | Yes |
| Temperature of cooled regenerated catalyst ° C. | | 460 |
| Pre-hydrocarbon pooling device | No | Yes |
| Temperature of pre-hydrocarbon pooling reaction ° C. | | 460 |
| Selectivity to low-carbon olefins ($C_2^=$ + $C_3^=$) % | 79.8 | 82.9 |

The invention claimed is:

1. A catalyst pre-hydrocarbon-pooling method, wherein a regenerated catalyst enters a pre-hydrocarbon-pooling reactor to undergo a pre-hydrocarbon pooling reaction with an activating medium to form "hydrocarbon pool" active species capable of having a good activity and good selectivity for catalyzing of a conversion reaction of an oxygenate to low-carbon olefin.

2. The method according to claim 1, wherein main operating conditions of the pre-hydrocarbon pooling reactor are a reaction temperature of 300-600° C. and contact time of less than 300 minutes.

3. The method according to claim 1, wherein main operating conditions of the pre-hydrocarbon-pooling reactor are a reaction temperature of 360-560° C. and contact time of 0.001-200 minutes.

4. The method according to claim 1, wherein main operating conditions of the pre-hydrocarbon-pooling reactor are a reaction temperature of 400-530° C. and contact time of 10-150 minutes.

5. The method according to claim 1, wherein the pre-hydrocarbon-pooling reactor adopts a low-velocity dense-phase fluidized bed having a superficial gas velocity of less than 0.5 m/s.

6. The method according to claim 1, wherein the pre-hydrocarbon-pooling reactor adopts a low-velocity dense-phase fluidized bed having a superficial gas velocity of 0.0001-0.3 m/s.

7. The method according to claim 1, wherein the pre-hydrocarbon-pooling reactor adopts a low-velocity dense-phase fluidized bed having a superficial gas velocity of 0.001-0.2 m/s.

8. The method according to claim 1, wherein the activing medium is any one, two or more of an oxygenate raw material, a reaction product, a hydrocarbon, and other oxygenates, or a mixture thereof, wherein: the oxygenate raw material is any one, two or more of methanol, ethanol, dimethyl ether, and methyl ethyl ether, or a mixture thereof; the reaction product is a reaction gas that has not undergone a separation or has been removed of part or all entrained catalyst by a first-stage separator or multiple stages of separators, or a reaction gas that has undergone heat exchanging, quenching, or water washing, or a reaction gas pressurized by a reaction gas compressor from a downstream olefin product separation unit, or a stripping gas from a top of a sewage stripper, or any one, two or more of the foregoing, or a mixture thereof, the hydrocarbon is any one, two or more of products from the downstream olefin product separation unit, including ethylene, propylene, ethane, propane, mixed $C_4$, $C_5^+$ fractions, and fuel gases, or a mixture thereof, or is any one, two or more of olefins, aromatic hydrocarbons, alkanes, or a mixture thereof; and the other oxygenates are any one, two or more of any organic oxygenates, or a mixture thereof.

9. The method according to claim 1, wherein the pre-hydrocarbon-pooling reactor is provided with an internal heat extractor or/and an external heat extractor.

10. A catalyst pre-hydrocarbon-pooling device, comprising a regenerated catalyst inlet, a regenerated catalyst outlet, an activating medium inlet, and an activating medium outlet, in which the "hydrocarbon pool" active species is formed by the catalyst pre-hydrocarbon-pooling method according to claim 1.

11. The device according to claim 10, further comprising an internal heat extractor or/and an external heat extractor.

12. The device according to claim 10, adopting any one, two or more of industrially used reactors including fluidized bed reactors, or a combination thereof, wherein the fluidized bed reactors include bubbling bed reactors, turbulent bed reactors, fast bed reactors, or riser reactors, and the like, wherein the riser reactors may be any industrially used equal-diameter or variable-diameter riser reactors.

13. The method according to claim 9, wherein a reaction temperature of the pre-hydrocarbon-pooling reactor is controlled mainly by adjusting an amount of the regenerated catalyst returned to the pre-hydrocarbon-pooling reactor, or/and a flow rate of a heat extracting medium or/and a flow rate of a fluidizing medium.

14. The method according to claim 2, wherein the pre-hydrocarbon-pooling reactor adopts a low-velocity dense-phase fluidized bed having a superficial gas velocity of less than 0.5 m/s.

15. The method according to claim 3, wherein the pre-hydrocarbon-pooling reactor adopts a low-velocity dense-phase fluidized bed having a superficial gas velocity of less than 0.5 m/s.

16. The method according to claim 4, wherein the pre-hydrocarbon-pooling reactor adopts a low-velocity dense-phase fluidized bed having a superficial gas velocity of less than 0.5 m/s.

17. The method according to claim 2, wherein the pre-hydrocarbon-pooling reactor adopts a low-velocity dense-phase fluidized bed having a superficial gas velocity of 0.0001-0.3 m/s.

18. The method according to claim 3, wherein the pre-hydrocarbon-pooling reactor adopts a low-velocity dense-phase fluidized bed having a superficial gas velocity of 0.0001-0.3 m/s.

19. The method according to claim 4, wherein the pre-hydrocarbon-pooling reactor adopts a low-velocity dense-phase fluidized bed having a superficial gas velocity of 0.0001-0.3 m/s.

* * * * *